US006864288B2

(12) United States Patent  (10) Patent No.: US 6,864,288 B2
Serhan  (45) Date of Patent: Mar. 8, 2005

(54) REGULATION OF PHOSPHOLIPASE D ACTIVITY

(75) Inventor: Charles N. Serhan, Needham, MA (US)

(73) Assignee: Brigham & Women's Hospital, Inc., Boston, MA (US)

( * ) Notice: Subject to any disclaimer, the term of this patent is extended or adjusted under 35 U.S.C. 154(b) by 119 days.

(21) Appl. No.: 10/004,155

(22) Filed: Oct. 19, 2001

(65) Prior Publication Data

US 2002/0120013 A1 Aug. 29, 2002

Related U.S. Application Data

(63) Continuation of application No. 09/525,157, filed on Mar. 14, 2000, now Pat. No. 6,353,026.
(60) Provisional application No. 60/125,194, filed on Mar. 18, 1999.

(51) Int. Cl.[7] .......................... A61K 31/23; A61K 31/20
(52) U.S. Cl. ....................... 514/552; 514/213; 514/219; 514/224; 514/558; 514/560
(58) Field of Search .............................. 514/213, 219, 514/224, 552, 558, 560

(56) References Cited

U.S. PATENT DOCUMENTS

| 5,441,951 A | * | 8/1995 | Serhan | ........................ 514/513 |
| 5,648,512 A | | 7/1997 | Serhan | ........................... 560/9 |
| 6,353,026 B1 | * | 3/2002 | Serhan | ........................ 514/560 |
| 6,720,354 B2 | * | 4/2004 | Serhan | ........................ 514/552 |

FOREIGN PATENT DOCUMENTS

| WO | WO 94/29262 | 12/1994 |
| WO | WO 95/01179 | 1/1995 |
| WO | WO 00/54767 | 9/2000 |

OTHER PUBLICATIONS

Olson et al., "Biochemistry and cell biology of phospholipase D in human neutrophils", Chemistry and Physics of Lipids, 80, pp. 3–19, 1996.*
Takano et al., "Neutrophil–mediated Changes in Vascular Permeability Are Inhibited by Topical Application of Aspirin–triggered 15–epi–lipoxin A4 and Novel Lipoxin B4 Stable Analogues", J. Clin. Invest. vol. 101, No. 4, Feb. 1998, pp. 819–826.*
Lloyd, A.R. et al., 1992. Poly's lament: the neglected role of the polymorphonuclear neutrophil in the afferent limb of the immune response. Immunology Today 13:169–172.*
Weissmann, G., Smolen, J. E., and Korchak, H. M. (1980) Release of inflammatory mediators from stimulated neutrophils. N. Engl. J. Med. 303, 27–34.
Serhan, C. N., Haeggstrom, J. Z., and Leslie, C. C. (1996) Lipid mediator networks in cell signaling: update and impact of cytokines. FASEB J. 10, 1147–1158.

Weiss, S. J. (1989) Tissue destruction by neutrophils, N. Engl. J. Med. 320, 365–376.
Serhan, C. N. (1994) Lipoxin biosynthesis and its impact in inflammatory and vascular events. Biochem. Biophys. Acta 1212, 1–25.
Borgeat, P., and Naccache, P. H. (1990) Biosynthesis and biological activity of leukotriene $B_4$. Clin. Biochem. 23, 459–468.
Yokomizo, T., Izumi, T., Chang, K., Takuwa, T., and Shimizu, T. (1997) A G–protein–coupled receptor for leukotriene $B_4$ that mediates chemotaxis. Nature 387, 620–624.
Fiore, S., Romano, M., Reardon, E. M., and Serhan, C. N. (1993) Induction of functional lipoxin $A_4$ receptors in HL–60 cells. Blood 81, 3395–3403.
Isakson, P., Seibert, K., Masferrer, J., Salvemini, D., Lee, L., and Needleman, P. (1995) Discovery of a better aspirin. Advances in Prostaglandin, Thromboxane & Leukotriene Research 23, 49–54.
Chiang, N., Takano, T., Clish, C. B., Petasis, N. A., Tai, H.–H., and Serhan, C. N. (1998) Aspirin–triggered 15–epi–lipoxin $A_4$ (ATL) generation by human leukocytes and murine peritonitis exudates: development of a specific 15–epi–$LXA_4$ ELISA. J. Pharmacol Exper. Ther. 287, 779–790.
Serhan, C. N., Maddox, J. F., Petasis, N. A., Akritopoulou–Zanze, I., Papayianni, A., Brady, H. R., Colgan, S. P., and Madara, J. L. (1995) Design of lipoxin $A_4$ stable analogs that block transmigration and adhesion of human neutrophils. Biochemistry 34, 14609–14615.
Takano, T., Fiore, S., Maddox, J. F., Brady, H. R., Petasis, N. A., and Serhan, C. N. (1997) Aspirin–triggered 15–epi–lipoxin $A_4$ ($LXA_4$) and $LXA_4$ Stable analogues are potent inhibitors of acute inflammation: Evidence for anti–inflammatory receptors. J. Exp. Med. 185, 1693–1704.
Owman, C., Garzino–Demo, A., Cocchi, F., Popovic, M., Sabirsh, A., and Gallo, R. (1998) The leukotriene $B_4$ receptor functions as a novel type of coreceptor mediating entry of primary HIV–1 isolates into CD4–positive cells. Proc. Natl. Acad. Sci. 95, 9530–9534.
Marcus, A. J. (1995) Aspirin as prophylaxis against colorectal cancer. N. Engl. J. Med. 333, 656–658.
Vainio, H., and Morgan, G. (1997) Aspirin for the second hundred years: new uses for an old drug. Pharmacol Toxicol 81, 151–152.
Herschman, H. R. (1998) Recent progress in the cellular and molecular biology of phostaglandin synthesis. Trends in Cardiovasc. Med. 8, 145–150.
Takano, T., Clish, C. B., Gronert, K., Petasis, N., and Serhan, C. N. (1998) Neutrophil–mediated changes in vascular permeability are inhibited by topical application of aspirin–triggered 15–epi–lipoxin $A_4$ and novel lipoxin $B_4$ stable analogues. J. Clin. Invest. 101, 819–826.

(List continued on next page.)

Primary Examiner—Dwayne Jones
(74) Attorney, Agent, or Firm—Dorsey & Whitney LLP; Scott D. Rothenberger

(57) ABSTRACT

Novel inhibitors of polyisoprenyl phosphate signaling regulates phopholipase D activity.

6 Claims, 3 Drawing Sheets

OTHER PUBLICATIONS

Billah, M. M., Eckel, S., Mullmann, T. J., Egan, R. W., and Siegel, M. I. (1989) Phosphatidylcholine hydrolysis by phospholipase D determines phosphatidate and diglyceride levels in chemotactic peptide–stimulated human neutrophils. Involvement of phsophatidate Phosphohydrolase in signal transduction. *J. Biol. Chem.* 264, 17069–17077.

Wakelam, M. J. O., Martin, A., Hodgkin, M. N., Brown, F., Pettit, T. R., Cross, M. J., De Takats, P. G., and Reynolds, J. L. (1997) Role and regulation of phospholipase D activity in normal and cancer cells. *Advances in Enzyme Regulation* 37, 29–34.

Olson, S. C., and Lambeth, J. D. (1996) Biochemistry and cell biology of phospholipase D in human neutrophils. *Chem. Phys. Lipids* 80, 3–19.

Steed, P. M., Clark, K. L., Boyar, W. C., and Lasala, D. J. (1998) Characterization of human PLD2 and the analysis of PLD isoform splice variants. *FASEB J.* 12, 1309–1317.

Martin, A., Saqib, K. M., Hodgkin, M. N., Brown, F. D., Pettit, T. R., Armstrong, S., and Wakelam, M. J. O. (1997) Role and regulation of phospholipase D signalling. *Biochem. Soc. Trans.* 25, 1157–1160.

Levy, B. D., Petasis, N. A., and Serhan, C. N. (1997) Polyisoprenyl phosphates in intracellular signalling. *Nature* 389, 985–989.

Agwu, D. E., McPhail, L. C., Sozzani, S., Bass, D. A., and McCall, C. E. (1991) Phosphatidic acid as a second messenger in human polymorphonuclear leukocytes. Effects on activation of NADPH oxidase. *J. Clin. Invest.* 88, 531–539.

Pettit, T. R., Martin, A., Horton, T., Liossis, C., Lord, J. M., and Wakelam, M. J. O. (1997) Diacylglycerol and phosphatidate generated by phospholipases C and D, respectively, have distinct fatty acid compositions and functions. *J. Biol. Chem.* 272, 17354–17359.

Gomez–Cambronero, J. (1995) Immunoprecipitation of a phospholipase D activity with antiphosphotyrosine antibodies. *J. Interferon Cytokine Res.* 15, 877–885.

Abousalham, A., Riviere, M., Teissere, M., and Verger, R. (1993) Improved purification and biochemical characterization of phospholipase D from cabbage. *Biochim. Biophys. Acta* 1158, 1–7.

Zhou, H.–L., Chabot–Fletcher, M., Foley, J. J., Sarau, H. M., Tzimas, M. N., Winkler, J. D., and Torphy, T. J. (1993) Association between leukotriene $B_4$–induced phospholipase D activation and degranulation of human neutrophils. *Biochem. Pharmacol.* 46, 139–148.

Shechter, I., Fogelman, A. M., and Popjak, G. (1980) A deficiency of mixed function oxidase activities in the cholesterol biosynthetic pathway of human granulocytes. *J. Lipid Res.* 21, 277–283.

Rabinowitz, J. L., Baker, D. G., Villanueva, T. G., Asanza, A. P., and Capuzzi, D. M. (1992) Liver lipid profiles of adults taking therapeutic doses of aspirin. *Lipids* 27, 311–314.

Claria, J., and Serhan, C. N. (1995) Aspirin triggers previously undescribed bioactive eicosanoids by human endothelial cell–leukocyte interactions. *Proc. Natl. Acad. Sci.* 92, 9475–9479.

Serhan, C. N. (1997) Lipoxins and Novel Aspirin–Triggered 15–epi–Lipoxins: A Jungle of Cell–Cell Interactions or a Therapeutic Opportunity? *Prostaglandins* 53, 107–137.

Exton, J. H. (1997) New developments in phospholipase D. *J. Biol. Chem.* 272, 15579–15582.

Fensome, A., Whatmore, J., Morgan, C., Jones, D., and Cockcroft, S. (1998) ADP–ribosylation factor and Rho proteins mediate fMLP–dependent activation of phospholipase D in human neutrophils. *J. Biol. Chem.* 273, 13157–13164.

Jarstfer, M. B., Blagg, B. S. J., Rogers, D. H., and Poulter, C. D. (1996) Biosynthesis of squalene. Evidence for a tertiary cyclopropylcarbinyl cationic intermediate in the rearrangement of presqualene diphosphate to squalene. *J. Amer. Chem. Soc.* 118, 13089–13090.

Bach, T. J. (1995) Some new aspects of isoprenoid biosynthesis in plants—a review. *Lipids* 30, 191–202.

Serhan et al., "Aspirin–Triggered 15–EPI–Lipoxin $A_4$ and Novel Lipoxin $B_4$ Stable Analogs Inhibit Neutrophil–Mediated Changes In Vascular Permeability", *Advances in Experimental Medicine and Biology*, vol. 469, 1999, pp. 287–293.

Gewirzt et al., "Pathogen–Induced Chemokine Secrection from Model Intestinal Epithelium is Inhibited by Lipoxin $A_4$ Analogs", *Journal of Clinical Investigation*, vol. 101, No. 9, May 1998, pp. 1860–1869.

Hansson et al., "Activation of Protein Kinase C By Lipoxin A and Other Eicosanoids. Intracellular Action of Oxygenation Products of Arachidonic Acid", *Biochemical and Biophysical Research Communications*, vol. 134, No. 3, 1986, pp. 1215–1222.

* cited by examiner

REGULATION OF PHOSPHOLIPASE D ACTIVITY

CROSS-REFERENCE TO RELATED APPLICATIONS

This application is a continuation application of U.S. patent application Ser. No. 09/525,157, filed Mar. 14, 2000, now U.S. Pat. No. 6,353,026 which in turn claims priority to U.S. Provisional Patent Application No. 60/125,194, filed Mar. 18, 1999, the contents of which are incorporated herein by reference.

STATEMENT REGARDING FEDERALLY SPONSORED RESEARCH

The work leading to this invention was supported in part by National Institutes of Health (NIH) grants GM-38765, DK-50305 and NHLBI-HL-56383. The U.S. Government therefore may have certain rights in the invention.

BACKGROUND OF THE INVENTION

Neutrophil (PMN) activation plays a central role in diverse host responses, such as host defense, inflammation and reperfusion injury (Weissmann, G., Smolen, J. E., and Korchak, H. M. (1980) Release of inflammatory mediators from stimulated neutrophils. *N. Engl. J. Med.* 303, 27–34). In response to inflammatory stimuli, PMN phospholipases are activated to remodel cell membranes and generate bioactive lipids that serve as intra- or extracellular mediators in the transduction of functional responses (Serhan, C. N., Haeggstrom, J. Z., and Leslie, C. C. (1996) Lipid mediator networks in cell signaling: update and impact of cytokines. *FASEB J.* 10, 1147–1158). Important components of microbicidal and acute inflammatory responses include reactive oxygen species and granule enzymes that are targeted to phagocytic vacuoles, but aberrant release of these potentially toxic agents can lead to amplification of inflammation as well as tissue injury and are implicated in a wide range of diseases (Weiss, S. J. (1989) Tissue destruction by neutrophils. *N. Engl. J. Med.* 320, 365–376). To prevent an over-exuberant inflammatory response and limit damage to the host, these PMFN programs are tightly regulated. The host mediators serving as endogenous anti-inflammatory or protective signals are only recently being appreciated (Serhan, C. N. (1994) Lipoxin biosynthesis and its impact in inflammatory and vascular events. *Biochim. Biophys. Acta* 1212, 1–25).

SUMMARY OF THE INVENTION

The present invention pertains to methods for modulating a disease or condition associated with phospholipase D (PLD) activity. The methods include administration to a subject, an effective anti-PLD amount of a lipoxin analog having the formula described infra, such that the PLD initiated activity is modulated.

The present invention also pertains to methods for treating phosphlipase D (PLD) activity in a subject. The methods include administration of an effective anti-PLD amount of a lipoxin analog described infra, such that PLD initiated activity is treated.

The present invention further pertains to methods for modulating a disease or condition associated with phospholipase D (PLD) initiated generation of superoxide or degranulation activity in a subject. The methods include, administration of an effective anti-PLD amount of a lipoxin analog described infra, such that a disease or condition associated with initiated by PLD generation of superoxide or degranulation activity, is modulated.

The present invention further relates to methods for treating phospholipase D (PLD) initiated superoxide generation or degranulation activity in a subject. The methods include administration of an effective anti-PLD amount of a lipoxin analog described infra, such that PLD initiated superoxide generation or degranulation activity is treated.

In preferred embodiments, the methods of the invention are performed in vitro or in vivo.

In another aspect, the present invention is directed to a packaged pharmaceutical composition for treating the activity or conditions listed above in a subject. The packaged pharmaceutical composition includes a container holding a therapeutically effective amount of at least one lipoxin compound having one of the formulae described infra and instructions for using the lipoxin compound for treating the activity or condition in the subject.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
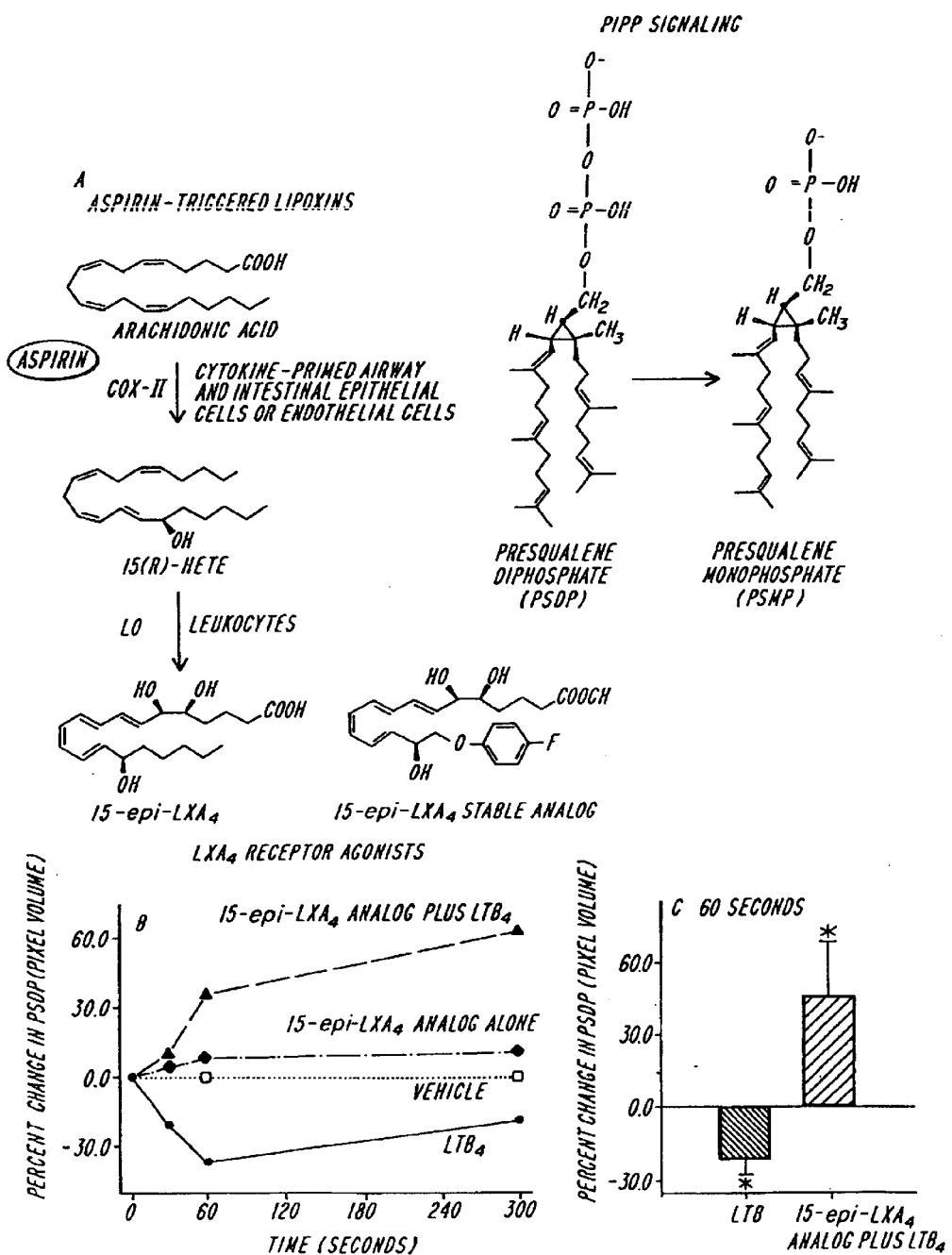
FIG. 1 shows that $LTB_4$ rapidly remodels PSDP in human PMN: biosynthetic switch by an aspirin-triggered $LXA_4$ analog. Panel A: Scheme for aspirin-triggered 15-epi-$LXA_4$ biosynthesis and structure of the stable analog, 15-epi-16-para-fluoro-phenoxy-$LXA_4$-methyl ester (15-epi-LXa) (left), and hypothetical scheme for PIPP signaling (right). PMN were labeled with $[\gamma\text{-}^{32}P]$-ATP and incubated (12.5× $10^6$ ml$^{-1}$, 37° C.) with $LTB_4$ (●, 100 nM), 15-epi-LXa (♦, 100 nM), vehicle (□, 0.1% ethanol) or 15-epi-LXa (100 nM, 5 min) followed by $LTB_4$ (▲, 100 nM). Non-saponifiable lipids were extracted and separated by TLC, and [$^{32}P$]-incorporation was quantitated by phosphoimaging (see Methods). Values are densitometric measurements. Panel B reports a representative time course (n=5), and Panel C shows the change (mean±S.E.) at 60 seconds. *P<0.05 by Student's t-test.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

It is of wide interest to understand how opposing extracellular signals (positive or negative) are translated into intracellular signaling events. Receptor-ligand interactions initiate the generation of bioactive lipids by human neutrophils (PMN) that serve as signals to orchestrate cellular responses important in host defense and inflammation. A novel polyisoprenyl phosphate (PIPP) signaling pathway was identified and it was found that one of its components, presqualene diphosphate (PSDP), is a potent negative intracellular signal in PMN that regulates superoxide anion generation by several stimuli including phosphatidic acid (Levy et al. (1998) Nature. 389, 985–990). It was determined intracellular PIPP signaling by autacoids with opposing actions on PMN—leukotriene $B_4$ ($LTB_4$), a potent chemoattractant, and lipoxin $A_4$ ($LXA_4$), a "stop signal" for recruitment. $LTB_4$ receptor activation initiated a rapid decrease in PSDP levels concurrent with activation of PLD and cellular responses. In sharp contrast, activation of the $LXA_4$ receptor reversed $LTB_4$-initiated PSDP remodeling leading to an accumulation of PSDP and potent inhibition of both PLD and superoxide anion generation. Thus, an inverse relationship was established for PSDP levels and PLD activity with two PMN ligands that evoke opposing responses. In addition, PSDP directly inhibited both isolated human recombinant (Ki=6 nM) and plant (Ki=20 nM) PLD. Together, these findings link PIPP remodeling to intracellular regulation of PMN function and suggest a role for PIPPs as lipid repressors in signal transduction, a novel mechanism that may also explain aspirin's suppressive actions in vivo in cell signaling.

Bioactive lipids are rapidly generated by activation of cell surface receptors that carry either specific positive or negative signals to modulate cellular responses. This is exemplified by the related eicosanoids, leukotriene $B_4$ ($LTB_4$), a potent chemoattractant (Borgeat, P., and Naccache, P. H. (1990) Biosynthesis and biological activity of leukotriene $B_4$. *Clin. Biochem*. 23, 459–468), and lipoxin $A_4$ ($LXA_4$), an endogenous "stop signal" for PMN recruitment (Serhan, C. N. (1994) Lipoxin biosynthesis and its impact in inflammatory and vascular events. *Biochim. Biophys. Acta* 1212, 1–25). $LTB_4$ and $LXA_4$ interact with highly specific and distinct G protein-coupled membrane receptors (Yokomizo, T., Izumi, T., Chang, K., Takuwa, T., and Shimizu, T. (1997) A G-protein-coupled receptor for leukotriene $B_4$ that mediates chemotaxis. *Nature* 387, 620–624; Fiore, S., Romano, M., Reardon, E. M., and Serhan, C. N. (1993) Induction of functional lipoxin $A_4$ receptors in HL-60 cells. *Blood* 81, 3395–3403). They each evoke opposing PMN responses, including $LXA_4$ inhibition of $LTB_4$-initiated chemotaxis, adhesion and transmigration (Serhan, C. N. (1994) Lipoxin biosynthesis and its impact in inflammatory and vascular events. *Biochim. Biophys. Acta* 1212, 1–25).

Abbreviations used throughout this application include: COX, cyclooxygenase; 15-epi-LX, 15-epimer lipoxin; 15-epi-LXa, 15-epi-16-para-fluoro-phenoxy $LXA_4$-methyl ester; FDP, farnesyl diphosphate; GST, glutathione-S-transferase; $LTB_4$, leukotriene $B_4$; LO, lipoxygenase; PA, phosphatidic acid; PC, phosphatidychloine; cPLD, cabbage phospholipase D; PIPP, polyisoprenyl phosphate; PMN, polymorphonuclear leukocytes; PSDP, presqualene diphosphate; PSMP, presqualene monophosphate; Sf9, *Spodoptera frugiperda*; TLC, thin-layer chromatography.

Aspirin is known to affect biosynthesis of lipid mediators and is widely used clinically for its anti-inflammatory properties. Mechanisms responsible for aspirin's anti-inflammatory actions remain of considerable interest. In particular, new "super-aspirins" are sought that spare the gastrointestinal tract and do not possess the deleterious side effects of steroids (Isakson, P., Seibert, K., Masferrer, J., Salvemini, D., Lee, L., and Needleman, P. (1995) Discovery of a better aspirin. *Advances in Prostaglandin, Thromboxane & Leukotriene Research* 23, 49–54). In one aspect it has been that, in addition to inhibiting prostanoid formation, aspirin triggers the endogenous generation of novel carbon 15 epimers of LX by transcellular routes (see FIG. 1A) during inflammation in vivo (e.g., between tissue resident cells and infiltrating leukocytes) (Chiang, N., Takano, T., Clish, C. B., Petasis, N. A., Tai, H. H., and Serhan, C. N. (1998) Aspirin-triggered 15-epi-lipoxin $A_4$ (ATL) generation by human leukocytes and murine peritonitis exudates: development of a specific 15-epi-$LXA_4$ ELISA. *J. Pharmacol Exper. Ther.* 287, 779–790). These aspirin-triggered lipoxins (15-epi-LX) are even more potent than the native LX as inhibitors of PMN responses, in part because they are active longer (Serhan, C. N., Maddox, J. F., Petasis, N. A., Akritopoulou-Zanze, I., Papayianni, A., Brady, H. R., Colgan, S. P., and Madara, J. L. (1995) Design of lipoxin $A_4$ stable analogs that block transmigration and adhesion of human neutrophils. *Biochemistry* 34, 14609–14615). PMN inhibition by LX and 15-epi-LX is evoked by specific receptor-activation of "inhibitory" signals and not via direct receptor level antagonism at $LTB_4$ receptors (Takano, T., Fiore, S., Maddox, J. F., Brady, H. R., Petasis, N. A., and Serhan, C. N. (1997) Aspirin-triggered 15-epi-lipoxin $A_4$ ($LXA_4$) and $LXA_4$ Stable analogues are potent inhibitors of acute inflammation: Evidence for anti-inflammatory receptors. *J. Exp. Med*. 185, 1693–1704). Moreover, interest in the regulation of the $LTB_4$ receptor is heightened by the recent finding that $LTB_4$ receptors also serve as novel HIV-1 coreceptors (Owman, C., Garzino-Demo, A., Cocchi, F., Popovic, M., Sabirsh, A., and Gallo, R. (1998) The leukotriene $B_4$ receptor functions as a novel type of coreceptor mediating entry of primary HIV-1 isolates into CD4-positive cells. *Proc. Natl. Acad. Sci.* 95, 9530–9534).

Despite ~100 years of use, complete knowledge of aspirin's therapeutic impact is still evolving with many newly discovered clinical utilities (Marcus, A. J. (1995) Aspirin as prophylaxis against colorectal cancer. *N. Engl. J. Med*. 333, 656–658). Regular ingestion of aspirin decreases the incidence of myocardial infarction, colorectal carcinoma and Alzheimer's disease (Vainio, H., and Morgan, G. (1997) Aspirin for the second hundred years: new uses for an old drug. *Pharmacol Toxicol* 81, 151–152), but side effects from aspirin, such as gastrointestinal ulceration, can limit its use. The recent discovery of a second isoform of cyclooxygenase (COX) that is induced during inflammation has led to a search for "super-aspirins" that can selectively inhibit COX-2 without disrupting the protective constitutive functions of COX-1 (Isakson, P., Seibert, K., Masferrer, J., Salvemini, D., Lee, L., and Needleman, P. (1995) Discovery of a better aspirin. *Advances in Prostaglandin, Thromboxane*

& *Leukotriene Research* 23, 49–54; Herschman, H. R. (1998) Recent progress in the cellular and molecular biology of prostaglandin synthesis. *Trends in Cardiovasc. Med.* 8, 145–150). Of particular interest in this regard, 15-epi-LX, which inhibit PMN migration, are endogenous products of aspirin's acetylating ability that may underly some of the salutary benefits of aspirin. Both LX and 15-epi-LX stable analogs were prepared, which like 15-epi-LXA$_4$, act via the LXA$_4$ receptor (Serhan, C. N., Maddox, J. F., Petasis, N. A., Akritopoulou-Zanze, I., Papayianni, A., Brady, H. R., Colgan, S. P., and Madara, J. L. (1995) Design of lipoxin A$_4$ stable analogs that block transmigration and adhesion of human neutrophils. *Biochemistry* 34, 14609–14615; Takano, T., Fiore, S., Maddox, J. F., Brady, H. R., Petasis, N. A., and Serhan, C. N. (1997) Aspirin-triggered 15-epi-lipoxin A$_4$ (LXA$_4$) and LXA$_4$ Stable analogues are potent inhibitors of acute inflammation: Evidence for anti-inflammatory receptors. *J. Exp. Med.* 185, 1693–1704). Suitable methods of preparation of lipoxin compounds can also be found, for example, in U.S. Pat. Nos. 5,411,951, 5,648,512, 5,650,435 and 5,750,354, incorporated herein by reference. For example, 15-epi-16-para-fluoro-phenoxy-lipoxin A$_4$-methyl ester (15-epi-LXa) is a synthetic analog of 15-epi-LXA$_4$ (FIG. 1A, bottom left) that not only resists rapid inactivation but acts topically to inhibit PMN infiltration and vascular permeability in mouse ear skin inflammation (Takano, T., Clish, C. B., Gronert, K., Petasis, N., and Serhan, C. N. (1998) Neutrophil-mediated changes in vascular permeability are inhibited by topical application of aspirin-triggered 15-epi-lipoxin A$_4$ and novel lipoxin B$_4$ stable analogues. *J. Clin. Invest.* 101, 819–826).

Elucidation of signaling pathway(s) responsible for receptor-operated blockage of PMN responses is of interest. Signaling via phospholipase D (PLD) plays a pivotal role in mounting cellular responses. Within seconds of exposure to ligands, PLD hydrolyzes membrane phosphatidylcholine (PC) to generate phosphatidic acid (PA) (Billah, M. M., Eckel, S., Mullmann, T. J., Egan, R. W., and Siegel, M. I. (1989) Phosphatidylcholine hydrolysis by phospholipase D determines phosphatidate and diglyceride levels in chemotactic peptide-stimulated human neutrophils. Involvement of phsophatidate phosphohydrolase in signal transduction. *J. Biol. Chem.* 264, 17069–17077). Formation of PA temporally antecedes functional responses, including vesicle secretion and assembly of the NADPH oxidase (Wakelam, M. J. O., Martin, A., Hodgkin, M. N., Brown, F., Pettit, T. R., Cross, M. J., De Takats, P. G., and Reynolds, J. L. (1997) Role and regulation of phospholipase D activity in normal and cancer cells. *Advances in Enzyme Regulation* 37, 29–34; Olson, S. C., and Lambeth, J. D. (1996) Biochemistry and cell biology of phospholipase D in human neutrophils. *Chem. Phys. Lipids* 80, 3–19). Several isozymes of PLD1 and PLD2 were cloned and characterized (Steed, P. M., Clark, K. L., Boyar, W. C., and Lasala, D. J. (1998) Characterization of human PLD2 and the analysis of PLD isoform splice variants. *FASEB J.* 12, 1309–1317), with PLD1b identified as a prominent isoform in human granulocytes (Martin, A., Saqib, K. M., Hodgkin, M. N., Brown, F. D., Pettit, T. R., Armstrong, S., and Wakelam, M. J. O. (1997) Role and regulation of phospholipase D signalling. *Biochem. Soc. Trans.* 25, 1157–1160). The complete DNA and amino acid sequences for human PLD is disclosed in Hammond et al. (1995) *J. Biol. Chem.* 270: 29640–29643, and Hammond et al. (1997) *J. Biol. Chem.* 272: 3860–3868, the entire contents of which are incorporated herein by reference, and can also be found at GenBank Accession Nos. NM 002662 and U38545.

Recently, a novel polyisoprenyl phosphate (PIPP) signaling pathway was identified (FIG. 1A) and found that, in PMN, presqualene diphosphate (PSDP) carries biological activity and serves as a negative intracellular signal that prevents superoxide anion generation by several stimuli including PA (Levy, B. D., Petasis, N. A., and Serhan, C. N. (1997) Polyisoprenyl phosphates in intracellular signalling. *Nature* 389, 985–989). Because PLD activation is linked to superoxide anion generation (Agwu, D. E., McPhail, L. C., Sozzani, S., Bass, D. A., and McCall, C. E. (1991) Phosphatidic acid as a second messenger in human polymorphonuclear leukocytes. Effects on activation of NADPH oxidase. *J. Clin. Invest.* 88, 531–539), it was determined that PIPP signaling also modulates phospholipase activity critical to global cellular activation. It was found that (i) that LTB$_4$ receptor activation rapidly degrades PSDP, a key component of PIPP signaling, that is reversed by a LXA$_4$ receptor agonist, (ii) that an aspirin-triggered 15-epi-LXA$_4$ stable analog potently inhibits LTB$_4$-initiated PLD activation and superoxide anion generation, and (iii) that PSDP directly inhibits both human recombinant and plant PLD. These findings provide evidence for receptor-initiated PIPP remodeling as a regulatory signaling pathway.

The present invention pertains to methods for modulating a disease or condition associated with phospholipase D (PLD) activity. The methods include administration to a subject, an effective anti-PLD amount of a lipoxin analog having the formula described infra, such that the PLD initiated activity is modulated.

The present invention also pertains to methods for treating phosphlipase D (PLD) activity in a subject. The methods include administration of an effective anti-PLD amount of a lipoxin analog described infra, such that PLD initiated activity is treated.

The present invention further pertains to methods for modulating a disease or condition associated with phospholipase D (PLD) initiated generation of superoxide or degranulation activity in a subject. The methods include, administration of an effective anti-PLD amount of a lipoxin analog described infra, such that a disease or condition associated with initiated by PLD generation of superoxide or degranulation activity, is modulated.

The present invention further relates to methods for treating phospholipase D (PLD) initiated superoxide generation or degranulation activity in a subject. The methods include administration of an effective anti-PLD amount of a lipoxin analog described infra, such that PLD initiated superoxide generation or degranulation activity is treated.

In preferred embodiments, the methods of the invention are performed in vitro or in vivo.

In another aspect, the present invention is directed to a packaged pharmaceutical composition for treating the activity or conditions listed above in a subject. The packaged pharmaceutical composition includes a container holding a therapeutically effective amount of at least one lipoxin compound having one of the formulae described infra and instructions for using the lipoxin compound for treating the activity or condition in the subject.

In one embodiment, compounds useful in the invention have the formula (I)

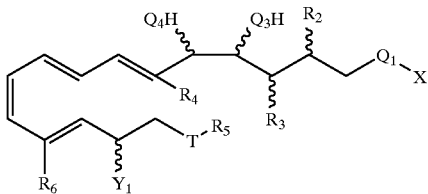

wherein X is $R_1$, $OR_1$, or $SR_1$;

wherein $R_1$ is
  (i) a hydrogen atom;
  (ii) an alkyl of 1 to 8 carbons atoms, inclusive, which may be straight chain or branched;
  (iii) a cycloalkyl of 3 to 10 carbon atoms;
  (iv) an aralkyl of 7 to 12 carbon atoms;
  (v) phenyl;
  (vi) substituted phenyl

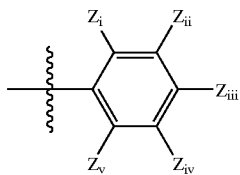

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
  (vii) a detectable label molecule; or
  (viii) a straight or branched chain alkenyl of 2 to 8 carbon atoms, inclusive;

wherein $Q_1$ is (C=O), $SO_2$ or (CN), provided when $Q_1$ is CN, then X is absent;

wherein $Q_3$ and $Q_4$ are each independently O, S or NH;

wherein one of $R_2$ and $R_3$ is a hydrogen atom and the other is
  (a) H;
  (b) an alkyl of 1 to 8 carbon atoms, inclusive, which may be a straight chain or branched;
  (c) a cycloalkyl of 3 to 6 carbon atoms, inclusive;
  (d) an alkenyl of 2 to 8 carbon atoms, inclusive, which may be straight chain or branched; or
  (e) $R_aQ_2R_b$ wherein $Q_2$ is —O— or —S—; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is
  (a) H;
  (b) an alkyl of 1 to 6 carbon atoms, inclusive, which may be a straight chain or branched;

wherein $R_5$ is

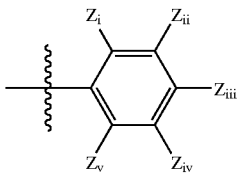

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is
  (a) H;
  (b) an alkyl from 1 to 4 carbon atoms, inclusive, straight chain or branched;

wherein T is O or S, and pharmaceutically acceptable salts thereof.

In another embodiment, compounds useful in the invention have the formula (II)

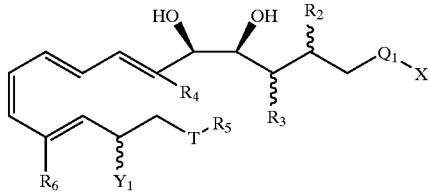

wherein X is $R_1$, $OR_1$, or $SR_1$;

wherein $R_1$ is
  (i) a hydrogen atom;
  (ii) an alkyl of 1 to 8 carbons atoms, inclusive, which may be straight chain or branched;
  (iii) a cycloalkyl of 3 to 10 carbon atoms;
  (iv) an aralkyl of 7 to 12 carbon atoms;
  (v) phenyl;
  (vi) substituted phenyl

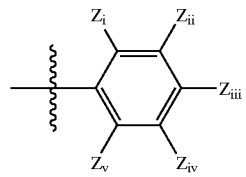

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
  (vii) a detectable label molecule; or
  (viii) a straight or branched chain alkenyl of 2 to 8 carbon atoms, inclusive;

wherein $Q_1$ is (C=O), $SO_2$ or (CN), provided when $Q_1$ is CN, then X is absent;

wherein one of $R_2$ and $R_3$ is a hydrogen atom and the other is
- (a) H;
- (b) an alkyl of 1 to 8 carbon atoms, inclusive, which may be a straight chain or branched;
- (c) a cycloalkyl of 3 to 6 carbon atoms, inclusive;
- (d) an alkenyl of 2 to 8 carbon atoms, inclusive, which may be straight chain or branched; or
- (e) $R_aQ_2R_b$ wherein $Q_2$ is —O— or —S—; wherein $R_a$ is alkylene of 0 to 6 carbons atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is
- (a) H;
- (b) an alkyl of 1 to 6 carbon atoms, inclusive, which may be a straight chain or branched;

wherein $R_5$ is

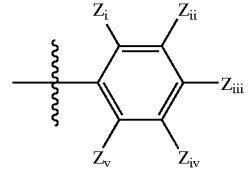

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is
- (a) H;
- (b) an alkyl from 1 to 4 carbon atoms, inclusive, straight chain or branched;

wherein T is O or S, and pharmaceutically acceptable salts thereof.

The invention is also directed to useful lipoxin compounds having the formula (III)

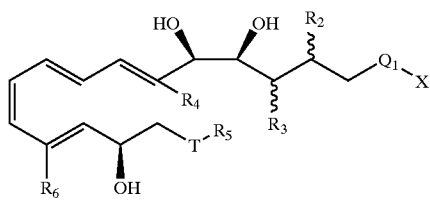

wherein X is $R_1$, $OR_1$ or $SR_1$;

wherein $R_1$ is
- (i) a hydrogen atom;
- (ii) an alkyl of 1 to 8 carbons atoms, inclusive, which may be straight chain or branched;
- (iii) a cycloalkyl of 3 to 10 carbon atoms;
- (iv) an aralkyl of 7 to 12 carbon atoms;
- (v) phenyl;
- (vi) substituted phenyl

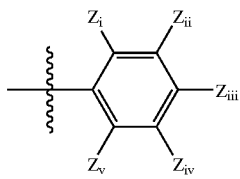

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
- (vii) a detectable label molecule; or
- (viii) a straight or branched chain alkenyl of 2 to 8 carbon atoms, inclusive;

wherein $Q_1$ is (C=O), $SO_2$ or (CN), provided when $Q_1$ is CN, then X is absent;

wherein one of $R_2$ and $R_3$ is a hydrogen atom and the other is
- (a) H;
- (b) an alkyl of 1 to 8 carbon atoms, inclusive, which may be a straight chain or branched;
- (c) a cycloalkyl of 3 to 6 carbon atoms, inclusive;
- (d) an alkenyl of 2 to 8 carbon atoms, inclusive, which may be straight chain or branched; or
- (e) $R_aQ_2R_b$ wherein $Q_2$ is —O— or —S—; wherein $R_a$ is alkylene of 0 to 6 carbons atoms, inclusive, which may be straight chain or branched and wherein $R_a$ is alkyl of 0 to 8 carbon atoms, inclusive, which may be straight chain or branched, provided when $R_b$ is 0, then $R_b$ is a hydrogen atom;

wherein $R_4$ is
- (a) H;
- (b) an alkyl of 1 to 6 carbon atoms, inclusive, which may be a straight chain or branched;

wherein $R_5$ is

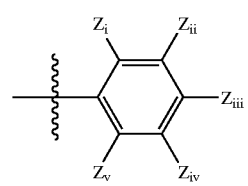

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $R_6$ is
- (a) H;
- (b) an alkyl from 1 to 4 carbon atoms, inclusive, straight chain or branched;

wherein T is O or S, and pharmaceutically acceptable salts thereof.

The invention is further directed to useful lipoxin compounds having the formula (IV)

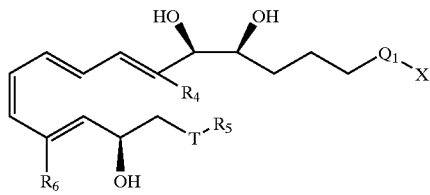

wherein X is $R_1$, $OR_1$, or $SR_1$;
wherein $R_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

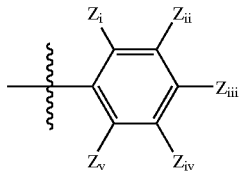

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$, is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $R_1$ is
(a) H;
(b) an alkyl of 1 to 6 carbon atoms, inclusive, which may be a straight chain or branched;
wherein $R_5$ is

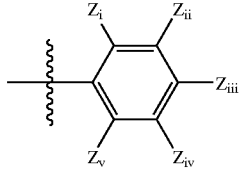

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$, is 1 to 8 carbon atoms, inclusive, which may be a straight chain or branched, and hydroxyl or a substituted or unsubstituted, branched or unbranched alkyl group;
wherein $R_6$ is
(a) H;
(b) an alkyl from 1 to 4 carbon atoms, inclusive, straight chain or branched;
wherein T is O or S, and pharmaceutically acceptable salts thereof.

The invention is further directed to useful lipoxin compounds having the formula (V)

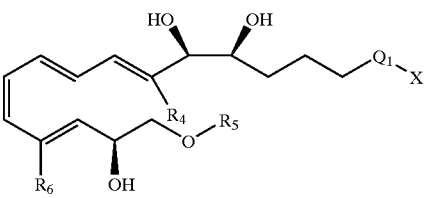

wherein X is $R_1$, $OR_1$, or $SR_1$;
wherein $R_1$ is
(i) a hydrogen atom;
(ii) an alkyl of 1 to 8 carbons atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

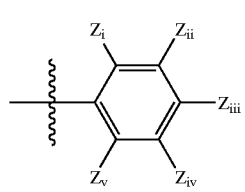

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $R_4$ is
(a) H;
(b) an alkyl of 1 to 6 carbon atoms, inclusive, which may be a straight chain or branched;
wherein $R_1$ is

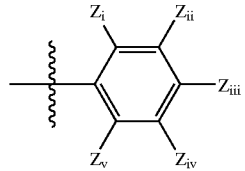

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;
wherein $R_6$ is
(a) H;
(b) an alkyl from 1 to 4 carbon atoms, inclusive, straight chain or branched; and
pharmaceutically acceptable salts thereof.

In preferred embodiments, X is $OR_1$ wherein $R_1$ is a hydrogen atom, an alkyl group of 1 to 4 carbon atoms or a pharmaceutically acceptable salt, $Q_1$ is C=O, $R_2$ and $R_3$, if present, are hydrogen atoms, $R_4$ is a hydrogen atom or methyl, $Q_3$ and $Q_4$, if present, are both O, $R_6$, if present, is a hydrogen atom, $Y_1$, if present, is OH, T is O and $R_5$ is a substituted phenyl, e.g.,

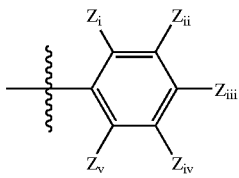

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$, is 1 to 8 carbon atoms, inclusive, which may be a straight chain or branched, and hydroxyl. In certain embodiments for $R_5$, para-fluorophenyl and/or unsubstituted phenyl are excluded, e.g., 15-epi-16-(para-fluoro)-phenoxy-$LXA_4$, 16-(para-fluoro)-phenoxy-$LXA_4$, 15-epi-16-phenoxy-$LXA_4$ or 16-phenoxy-$LXA_4$. The compounds encompassed by U.S. Pat. No. 5,441,951 are excluded from certain aspects of the present invention.

In still another aspect, the present invention is directed to pharmaceutical compositions including compounds having the above-described formulae and a pharmaceutically acceptable carrier. In one embodiment, a preferred compound is

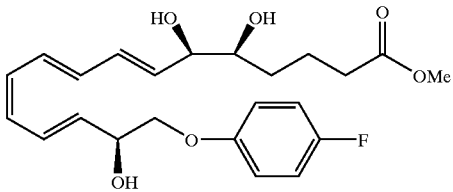

In a preferred embodiment, the pharmaceutical carrier is not a ketone, e.g., acetone.

In preferred embodiments, $Y_1$ is a hydroxyl and the carbon bearing the hydroxyl can have an R or S configuration. In most preferred embodiments, the chiral carbon bearing the hydroxyl group, e.g., $Y_1$, is designated as a 15-epi-lipoxin as is known in the art.

In certain embodiments the chirality of the carbons bearing the $R_2$, $R_3$, $Q_3$ and $Q_4$ groups can each independently be either R or S. In preferred embodiments, $Q_3$ and $Q_4$ have the chiralities shown in structures II, III, IV or V.

In preferred embodiments, $R_4$ is a hydrogen. In other preferred embodiments, $R_6$ is a hydrogen.

Additionally, $R_5$ can be a substituted or unsubstituted, branched or unbranched alkyl group having between 1 and about 6 carbon atoms, preferably between 1 and 4 carbon atoms, most preferably between 1 and 3, and preferably one or two carbon atoms. The carbon atoms can have substituents which include halogen atoms, hydroxyl groups, or ether groups.

The compounds useful in the present invention can be prepared by the following synthetic scheme:

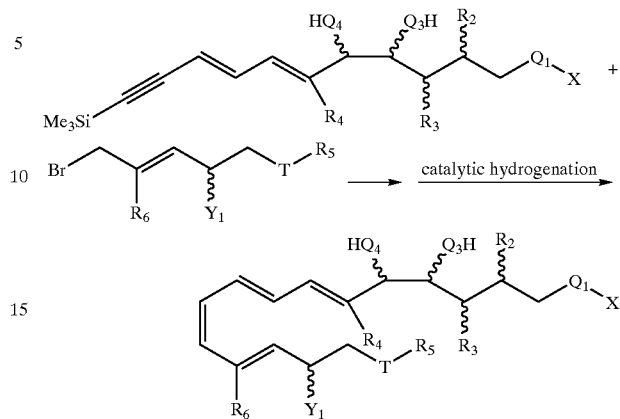

wherein X, $Q_1$, $Q_3$, $Q_4$, $R_2$, $R_3$, $R_4$, $R_5$, $R_6$, $Y_1$ and T are as defined above. Suitable methods known in the art to can be used to produce each fragment. For example, the acetylenic fragment can be prepared by the methods discussed in Nicolaou, K. C. et al. (1991) Angew. Chem. Int. Ed. Engl. 30:1100; Nicolaou, K. C. et al. (1989) J. Org. Chem. 54:5527; Webber, S. E. et al. (1988) Adv. Exp. Med. Biol. 229:61; and U.S. Pat. No. 5,441,951. The second fragment can be prepared by the methods of Raduchel, B. and Vorbruggen, H. (1985) Adv. Prostaglandin Thromboxane Leukotriene Res. 14:263.

A "lipoxin analog" shall mean a compound which has an "active region" that functions like the active region of a "natural lipoxin", but which has a "metabolic transformation region" that differs from natural lipoxin. Lipoxin analogs include compounds which are structurally similar to a natural lipoxin, compounds which share the same receptor recognition site, compounds which share the same or similar lipoxin metabolic transformation region as lipoxin, and compounds which are art-recognized as being analogs of lipoxin. Lipoxin analogs include lipoxin analog metabolites. The compounds disclosed herein may contain one or more centers of asymmetry. Where asymmetric carbon atoms are present, more than one stereoisomer is possible, and all possible isomeric forms are intended to be included within the structural representations shown. Optically active (R) and (S) isomers may be resolved using conventional techniques known to the ordinarily skilled artisan. The present invention is intended to include the possible diastereiomers as well as the racemic and optically resolved isomers.

The terms "corresponding lipoxin" and "natural lipoxin" refer to a naturally-occurring lipoxin or lipoxin metabolite. Where an analog has activity for a lipoxin-specific receptor, the corresponding or natural lipoxin is the normal ligand for that receptor. For example, where an analog is a $LXA_4$ specific receptor on differentiated HL-60 cells, the corresponding lipoxin is $LXA_4$. Where an analog has activity as an antagonist to another compound (such as a leukotriene), which is antagonized by a naturally-occurring lipoxin, that natural lipoxin is the corresponding lipoxin.

"Active region" shall mean the region of a natural lipoxin or lipoxin analog, which is associated with in vivo cellular interactions. The active region may bind the "recognition site" of a cellular lipoxin receptor or a macromolecule or complex of macromolecules, including an enzyme and its cofactor. Preferred lipoxin $A_4$ analogs have an active region comprising $C_5$–$C_{15}$ of natural lipoxin $A_4$. Preferred lipoxin $B_4$ analogs have an active region comprising C5–C14 of natural lipoxin B4.

The term "recognition site" or receptor is art-recognized and is intended to refer generally to a functional macromolecule or complex of macromolecules with which certain groups of cellular messengers, such as hormones, leukotrienes, and lipoxins, must first interact before the biochemical and physiological responses to those messengers are initiated. As used in this application, a receptor may be isolated, on an intact or permeabilized cell, or in tissue, including an organ. A receptor may be from or in a living subject, or it may be cloned. A receptor may normally exist or it may be induced by a disease state, by an injury, or by artificial means. A compound of this invention may bind reversibly, irreversibly, competitively, noncompetitively, or uncompetitively with respect to the natural substrate of a recognition site.

The term "metabolic transformation region" is intended to refer generally to that portion of a lipoxin, a lipoxin metabolite, or lipoxin analog including a lipoxin analog metabolite, upon which an enzyme or an enzyme and its cofactor attempts to perform one or more metabolic transformations which that enzyme or enzyme and cofactor normally transform on lipoxins. The metabolic transformation region may or may not be susceptible to the transformation. A nonlimiting example of a metabolic transformation region of a lipoxin is a portion of $LXA_4$ that includes the C-13,14 double bond or the C-15 hydroxyl group, or both.

The term "detectable label molecule" is meant to include fluorescent, phosphorescent, and radiolabeled molecules used to trace, track, or identify the compound or receptor recognition site to which the detectable label molecule is bound. The label molecule may be detected by any of the several methods known in the art.

The term "labeled lipoxin analog" is further understood to encompass compounds which are labeled with radioactive isotopes, such as but not limited to tritium ($^3$H), deuterium ($^2$H), carbon ($^{14}$C), or otherwise labeled (e.g. fluorescently). The compounds of this invention may be labeled or derivatized, for example, for kinetic binding experiments, for further elucidating metabolic pathways and enzymatic mechanisms, or for characterization by methods known in the art of analytical chemistry.

The term "inhibits metabolism" means the blocking or reduction of activity of an enzyme which metabolizes a native lipoxin. The blockage or reduction may occur by covalent bonding, by irreversible binding, by reversible binding which has a practical effect of irreversible binding, or by any other means which prevents the enzyme from operating in its usual manner on another lipoxin analog, including a lipoxin analog metabolite, a lipoxin, or a lipoxin metabolite.

The term "resists metabolism" is meant to include failing to undergo one or more of the metabolic degradative transformations by at least one of the enzymes which metabolize lipoxins. Two nonlimiting examples of $LXA_4$ analog that resists metabolism are 1) a structure which can not be oxidized to the 15-oxo form, and 2) a structure which may be oxidized to the 15-oxo form, but is not susceptible to enzymatic reduction to the 13,14-dihydro form.

The term "more slowly undergoes metabolism" means having slower reaction kinetics, or requiring more time for the completion of the series of metabolic transformations by one or more of the enzymes which metabolize lipoxin. A nonlimiting example of a $LXA_4$ analog which more slowly undergoes metabolism is a structure which has a higher transition state energy for C-15 dehydrogenation than does $LXA_4$ because the analog is sterically hindered at the C-16.

The term "tissue" is intended to include intact cells, blood, blood preparations such as plasma and serum, bones, joints, muscles, smooth muscles, and organs.

The term "halogen" is meant to include fluorine, chlorine, bromine and iodine, or fluoro, chloro, bromo, and iodo. In certain aspects, the compounds of the invention do not include halogenated compounds, e.g., fluorinated compounds.

The term "subject" is intended to include living organisms susceptible to conditions or diseases caused or contributed to by inflammation, inflammatory responses, vasoconstriction, and myeloid suppression. Examples of subjects include humans, dogs, cats, cows, goats, and mice. The term subject is further intended to include transgenic species.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiment, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters. In a preferred embodiment, the ester is not a methyl ester (See, for example, Berge et al., supra.).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Methods

Materials.

15-epi-LXa, PSDP and PSMP were prepared by total organic synthesis and characterized by their physical chemical and biological properties (Takano, T., Clish, C. B., Gronert, K., Petasis, N., and Serhan, C. N. (1998) Neutrophil-mediated changes in vascular permeability are inhibited by topical application of aspirin-triggered 15-epi-lipoxin $A_4$ and novel lipoxin $B_4$ stable analogues. *J. Clin. Invest.* 101, 819–826; Levy, B. D., Petasis, N. A., and Serhan, C. N. (1997) Polyisoprenyl phosphates in intracellular signaling. *Nature* 389, 985–989). $LTB_4$ was purchased from Cayman Chemical (Ann Arbor, Mich.), cabbage PLD (cPLD), FDP, squalene, lysis buffer reagents and cytochrome c were from Sigma Chemical Co. (St. Louis, Mo.), and PC and PA were from Avanti Polar Lipids (Alabaster, Ala.). The integrity and concentration of each bioactive lipid was assessed just prior to each series of experiments by UV analysis (eicosanoids and analogs) and phosphorus determinations (polyisoprenyl phosphates) (Takano, T., Clish, C. B., Gronert, K., Petasis, N., and Serhan, C. N. (1998) Neutrophil-mediated changes in vascular permeability are inhibited by topical application of aspirin-triggered 15-epi-lipoxin $A_4$ and novel lipoxin $B_4$ stable analogues. *J. Clin. Invest.* 101, 819–826; Levy, B. D., Petasis, N. A., and Serhan, C. N. (1997) Polyisoprenyl phosphates in intracellular signaling. *Nature* 389, 985–989).

Human PMN

Peripheral venous blood (~180 ml) was obtained by venipuncture from healthy volunteers who denied taking any medication for at least two weeks and had given written informed consent to a protocol approved by Brighamn and Women's Hospital's Human Research Committee. PMN were isolated from whole blood and steady state labeled with $[\gamma-^{32}P]ATP$ (40 $\mu Ciml^{-1}$, 90 min, 37° C.) as in (Levy, B. D., Petasis, N. A., and Serhan, C. N. (1997) Polyisoprenyl phosphates in intracellular signalling. *Nature* 389, 985–989). Labeled PMN were resuspended ($20 \times 10^6$ $ml^{-1}$ PBS with 1 mM $CaCl_2$, pH 7.40) and exposed to $LTB_4$ (100 nM), 15-epi-LXa (100 nM) or vehicle (0.1% EtOH) for 0 to 300 seconds (37° C.). From each incubation, aliquots were removed at indicated intervals to determine the radiolabeling of nonsaponifiable lipids ($10–12 \times 10^6$ PMN) and PLD activity ($1–1.25 \times 10^6$ PMN). Materials present in each incubation were saponified, extracted and separated by TLC with phosphoimaging (model 425E and integration software; Molecular Dynamics), which was used for PSDP mass determination as in ref 22.

Preparation of Recombinant Human PLD1b.

*Spodoptera frugiperda* (Sf9) cells were cultured in suspension at $2 \times 10^5$ to $2 \times 10^6$ cells/ml TC 100 medium supplemented with 10% fetal calf serum (Gibco). A cDNA encoding human PLD1b (cloned from placental tissue) was inserted into the transfer vector pACGHLT (Pharmingen) downstream of, and in frame with, vector sequences encoding glutathione-S-transferase (GST), hexahistidine, a protein kinase A phosphorylation site and a thrombin cleavage site. The GST-hPLD1b construct was cotransfected into Sf9 cells with linearized, polyhedrin-minus (PH-), AcMNPV DNA, Bac-N-Blue, according to the supplier's instructions (Invitrogen). Homologous recombination between linearized virus and the transfer vector restored the function of essential viral gene ORF1629 to yield infectious, recombinant virus. After two rounds of plaque-purification, recombinant virus was amplified by large scale infections of Sf9 cells until a titer of $8 \times 10^7$ pfu/ml was obtained. To generate GST-hPLD1b, 500 ml of Sf9 cells at $2 \times 10^6$ cells/ml were infected with virus at a multiplicity of infection of 10:1. Cells were harvested 72 hours post-infection, lysed and the expressed GST-hPLD1b purified on glutathione agarose beads, according to supplier's instructions (Pharmingen). The purified recombinant protein was identified by immunoreactivity with goat anti-GST pAb (Amersham Pharmacia Biotech) and rabbit pAb raised against the PLD consensus peptide sequence GSANIN (gift of P. Parker, ICRF, London, UK), and by activity in an in vitro PLD assay (24).

PLD Activity and Superoxide Anion Generation

Lysates were generated from cells at rest or after exposure to agonist using a lysis buffer comprised of 0.1 M Hepes (pH 7.4), 0.7 mM sodium orthovanadate, 10 $\mu$M p-nitrophenylphosphate, 10 mM EGTA, 5.5% triton X-100, 0.5 M β-glycerophosphate, 10 mM phenylmethylsulfonyl-fluoride, 0.1 mM ammonium molybdate, 12 mM DFP, 5 $\mu gml^{-1}$ leupeptin, 2 $\mu gml^{-1}$ aprotinin and 7 $\mu gml^{-1}$ pepstatin A (as in ref 25) and utilized for bioassay.

PMN lysates (90–130 $\mu$g protein), purified phospholipase D (3–30 units) (EC 3.1.4.4., Sigma Chemical Co.) or recombinant hPLD1b were warmed (37° C. for mammalian enzyme and 30° C. for cabbage, 3 min) and exposed to PSDP, PSMP or FDP (10–1000 nM, 5 min, 37° C. or 30° C.) followed by PC (0.5 to 5 mM) in Tris-HCl (50 mM pH 7.5) with $CaCl_2$ (30 mM). Reactions were terminated at 30 second intervals (0–90 seconds) with Tris-HCl (1 M) plus EDTA (50 mM). Choline release was quantitated as in ref 26.

Freshly isolated human PMN ($1-3 \times 10^6$ PMN/ml HBSS+ 1.6 mM $CaCl_2$) were incubated (5 min, 37° C.) in the presence of 15-epi-LXa (1–100 nM) or vehicle (0.1% ethanol), and then exposed (10 min) to $LTB_4$ (100 nM) in the presence of cytochrome c (7 mg/ml). Superoxide anion generation was determined as in ref 22.

Statistical Analysis

Results are expressed as the mean±S.E. and statistical significance was evaluated using the Student's t test.

Results

Leukotriene $B_4$ Stimulates Rapid Remodeling of PIPP: Degradation of PSDP.

Leukotriene $B_4$ interacts with its receptor to rapidly activate phospholipases and signal cellular responses (Yokomizo, T., Izumi, T., Chang, K., Takuwa, T., and Shimizu, T. (1997) A G-protein-coupled receptor for leukotriene $B_4$ that mediates chemotaxis. Nature 387, 620–624). To determine if $LTB_4$ receptor activation lead to remodeling of PIPP and specifically PSDP, cellular phosphate pools were steady state labeled with [$\gamma$-$^{32}$P]-ATP (see Methods) and exposed to either $LTB_4$ (100 nM) or vehicle (0.1% ethanol) alone. Aliquots were removed at timed intervals from 0 to 300 sec (37° C.) and non-saponifiable phosphorylated lipids were isolated and quantitated by phosphoimager for [$^{32}$P] incorporation. PSDP levels in unstimulated PMN are ~1.7 nmoles/$10^7$ PMN (~50 nM) (Levy, B. D., Petasis, N. A., and Serhan, C. N. (1997) Polyisoprenyl phosphates in intracellular signalling. Nature 389, 985–989). PSDP and presqualene monophosphate (PSMP), but not farnesyl diphosphate (FDP), incorporated [$^{32}$P] from ATP, consistent with recent evidence (Levy, B. D., Petasis, N. A., and Serhan, C. N. (1997) Polyisoprenyl phosphates in intracellular signalling. Nature 389, 985–989). $LTB_4$ initiated a rapid (evident within 30 sec) (FIG. 1B) and statistically significant decrease in [$^{32}$P]-PSDP (28%) within 60 sec (FIG. 1C). Within the ensuing 270 sec, [$^{32}$P]-PSDP levels returned to baseline amounts (t=0). Changes in [$^{32}$P]-PSDP after $LTB_4$ receptor activation reflected changes in PSDP mass. These results confirmed that PSDP was present in PMN (Levy, B. D., Petasis, N. A., and Serhan, C. N. (1997) Polyisoprenyl phosphates in intracellular signalling. Nature 389, 985–989) and indicated that $LTB_4$ initiated a marked decrement in PSDP (FIG. 1) with a time course of PIPP remodeling concurrent with $LTB_4$ kinetics of cellular activation (Borgeat, P., and Naccache, P. H. (1990) Biosynthesis and biological activity of leukotriene $B_4$. Clin. Biochem. 23, 459–468; Levy, B. D., Petasis, N. A., and Serhan, C. N. (1997) Polyisoprenyl phosphates in intracellular signalling. Nature 389, 985–989).

15-epimer LX Analog Switches the $LTB_4$ Program to Enhance PSDP

Both $LXA_4$ and some 15-epi-$LXA_4$ stable analogs act at the $LXA_4$ receptor on PMN, inhibiting infiltration in vivo. To determine if LX and 15-epi-LX mediate inhibitory actions via PIPP signaling, the impact of a 15-epi-$LXA_4$ analog (15-epi-LXa) (100 nM, 5 min, 37° C.) on $LTB_4$ (100 nM)-stimulated changes in PSDP was examined using [$^{32}$P] labeling of PMN lipids (vide supra, in parallel incubations). Alone, 15-epi-LXa did not affect the rate of PIPP remodeling (FIG. 1B). Of interest, exposure to $LTB_4$ in the presence of equimolar 15-epi-LXa not only prevented the $LTB_4$ initiated decrease in PSDP, but additionally stimulated a significant increase (~72%) in [$^{32}$P]-PSDP at 60 sec (FIG. 1C). PSDP levels continued to rise for at least 300 sec after exposure to $LTB_4$ (FIG. 1B). Native $LXA_4$ and its related $LXA_4$ receptor agonist, 16-phenoxy-$LXA_4$-methyl ester, gave qualitatively similar responses as 15-epi-LXa with a rank order of potency of 15-epi-LXa>16-phenoxy-$LXA_4$>$LXA_4$ with 15-epi-LXa 1–2 orders of magnitude more potent. These results indicate that 15-epi-LXa, which inhibits $LTB_4$ responses in vivo (Takano, T., Fiore, S., Maddox, J. F., Brady, H. R., Petasis, N. A., and Serhan, C. N. (1997) Aspirin-triggered 15-epi-lipoxin $A_4$ ($LXA_4$) and $LXA_4$ Stable analogues are potent inhibitors of acute inflammation: Evidence for anti-inflammatory receptors. J. Exp. Med. 185, 1693–1704), dramatically switches $LTB_4$-initiated PIPP signaling. Moreover, increases in PSDP levels evoked by coactivation of the $LXA_4$ and $LTB_4$ receptors indicate that the time course of PSDP accumulation correlated with regulation of $LTB_4$'s actions by LX and 15-epi-LXa (vide infra).

15-epi-LXa Inhibits $LTB_4$-stimulated PLD Activity and $O_2^-$ Generation $LTB_4$-stimulated PLD activity is associated with morphologic change, degranulation and $O_2^-$ production in PMN (Olson, S. C., and Lambeth, J. D. (1996) Biochemistry and cell biology of phospholipase D in human neutrophils. Chem. Phys. Lipids 80, 3–19; Zhou, H. -L., Chabot-Fletcher, M., Foley, J. J., Sarau, H. M., Tzimas, M. N., Winkler, J. D., and Torphy, T. J. (1993) Association between leukotriene $B_4$-induced phospholipase D activation and degranulation of human neutrophils. Biochem. Pharmacol. 46, 139–148). To determine whether LT and LX-mediated remodeling of PIPP correlates with specific cell signaling events, PLD activity was monitored in cell lysates from the same incubations used in FIG. 1. $LTB_4$ gave increases in PLD activity that were maximal by 60 sec (FIG. 2A). These values for $LTB_4$ and PLD are consistent with those of earlier reports (Gomez-Cambronero, J. (1995) Immunoprecipitation of a phospholipase D activity with antiphosphotyrosine antibodies. J. Interferon Cytokine Res. 15, 877–885; Zhou, H. -L., Chabot-Fletcher, M., Foley, J. J., Sarau, H. M., Tzimas, M. N., Winkler, J. D., and Torphy, T. J. (1993) Association between leukotriene $B_4$-induced phospholipase D activation and degranulation of human neutrophils. Biochem. Pharmacol. 46, 139–148). In the presence of 15-epi-LXa, $LTB_4$-stimulated PLD activity was inhibited (~81%) at 60 sec (FIGS. 2A&B). 15-epi-LXa also potently inhibited $LTB_4$-stimulated $O_2^-$ generation (FIG. 2C). Together, these findings indicate that ligand-receptor interaction that signals opposing cellular responses gave an inverse relationship between [$^{32}$P]-PSDP levels and PLD activity, demonstrating that PSDP could regulate PLD.

Direct Inhibition of Both Plant and Mammalian PLD.

Figure 3:
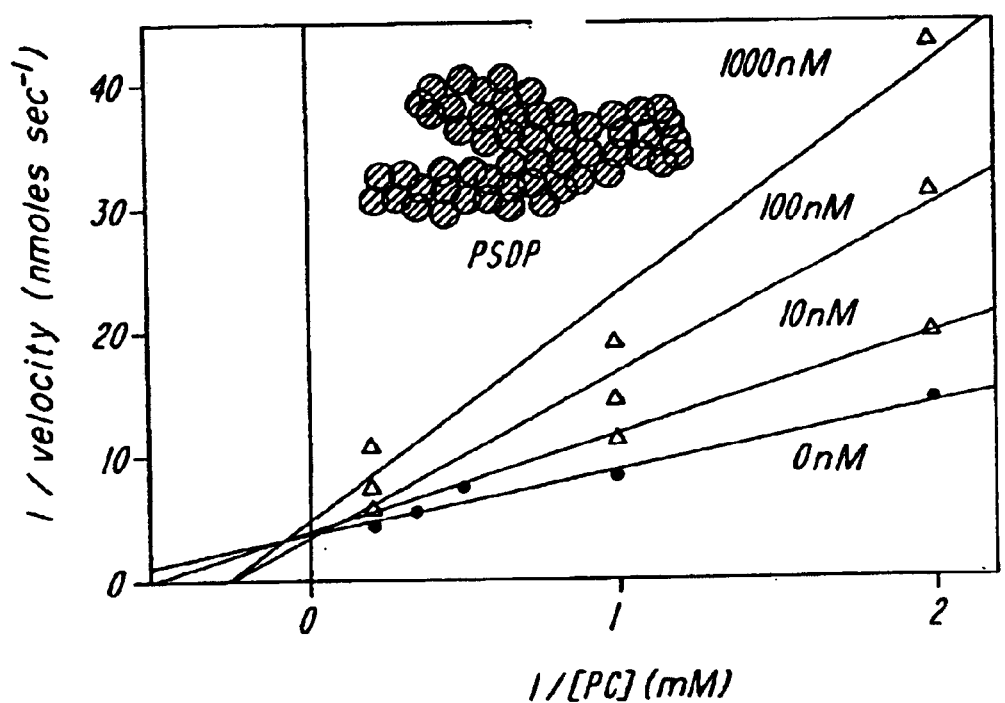
FIG. 3 demonstrates PSDP inhibits phospholipase D. Purified PLD (3 units EC 3.1.4.4./125 μl) was warmed (3 min, 30° C.) and exposed to PSDP (10–1000 nM, 5 min, 30° C.) or vehicle (0.04% ethanol final conc.) followed by PC (0.5–5 mM) in 50 mM Tris-HCl (pH 7.5) plus 30 mM $CaCl_2$. Reactions were terminated at 30 sec intervals and choline release quantitated as in FIG. 2 legend. Values represent the mean for n≧4 for reactions in the absence of PSDP (●, $r^2$=0.963) and the mean for n≧3 with PSDP (Δ, $r^2$=0.995, 0.971 and 0.953 for 10, 100 and 1000 nM, respectively). CS Chem3D Pro software (CambridgeSoft Corp., Cambridge, Mass.) was used to calculate an energy minimized model of PSDP (inset).

To determine whether polyisoprenyl phosphates act directly on PLD, PSDP and closely related lipids were incubated with purified plant enzyme (EC 3.1.4.4; Vm=0.29 nmoles/sec, Km=1.4 mM). As seen in FIG. 3, PSDP inhibited cPLD in a concentration-dependent fashion (10 to 1000 nM) with a Ki of 20 nM ((PSDP)=10 nM). Lineweaver-burk analyses (FIG. 3) were consistent with a competitive inhibition model. Closely related lipids, such as PSMP (minus only one phosphate), showed a greater than 100-fold loss in inhibitory potency compared to PSDP (Table I). Comparable inhibition was not evident with other polyisoprenoids (i.e., FDP and squalene) or a PLD product (PA). It was determined whether PSDP could also inhibit mammalian PLD by determining recombinant human PLD1b kinetics in vitro with PSDP. The recombinant enzyme (Vm=0.36 nmoles/sec, Km=13.8 mM) was also dramatically inhibited by PSDP with a Ki of 6 nM (Table I).

TABLE 1

PSDP selectively inhibits phospholipase D: structure activity relationship with related endogenous lipids[a]

| Lipid | Enzyme | $K_m$ (mM) | $V_m$ | $K_i$ (nM) |
|---|---|---|---|---|
| | cPLD | 1.4 | 0.29 | |
| | rhPLD1b | 13.8 | 0.36 | |
| | | $K_{m\ app}$ (mM) | $V_{m\ app}$ | |
| Presqualene diphosphate | cPLD | 2.1 | 0.25 | 20 |
| | rhPLD1b | 3.1 | 0.03 | 6 |
| Presqualene monophosphate | cPLD | 3.1 | 0.36 | 3210 |
| Squalene | cPLD | 4.0 | 0.46 | 0 |
| Farnesyl diphosphate | cPLD | 0.9 | 0.25 | 0 |
| Phosphatidic acid | cPLD | 3.6 | 0.43 | 0 |

[a]Enzyme kinetics for PLD were determined in the presence of PSDP or related lipids. Purified or isolated PLD (3u cPLD or 0.3 u rhPLD1b/reaction) activity in the presence of the test compounds was determined as described in FIG. 3 legend ($n \geq 3$). $K_i$ was calculated using the formula: Slope = $K_m/V_m$ (1 + [I]/$K_i$). Absence of inhibition is reported as $K_i = 0$.

Figure 2:
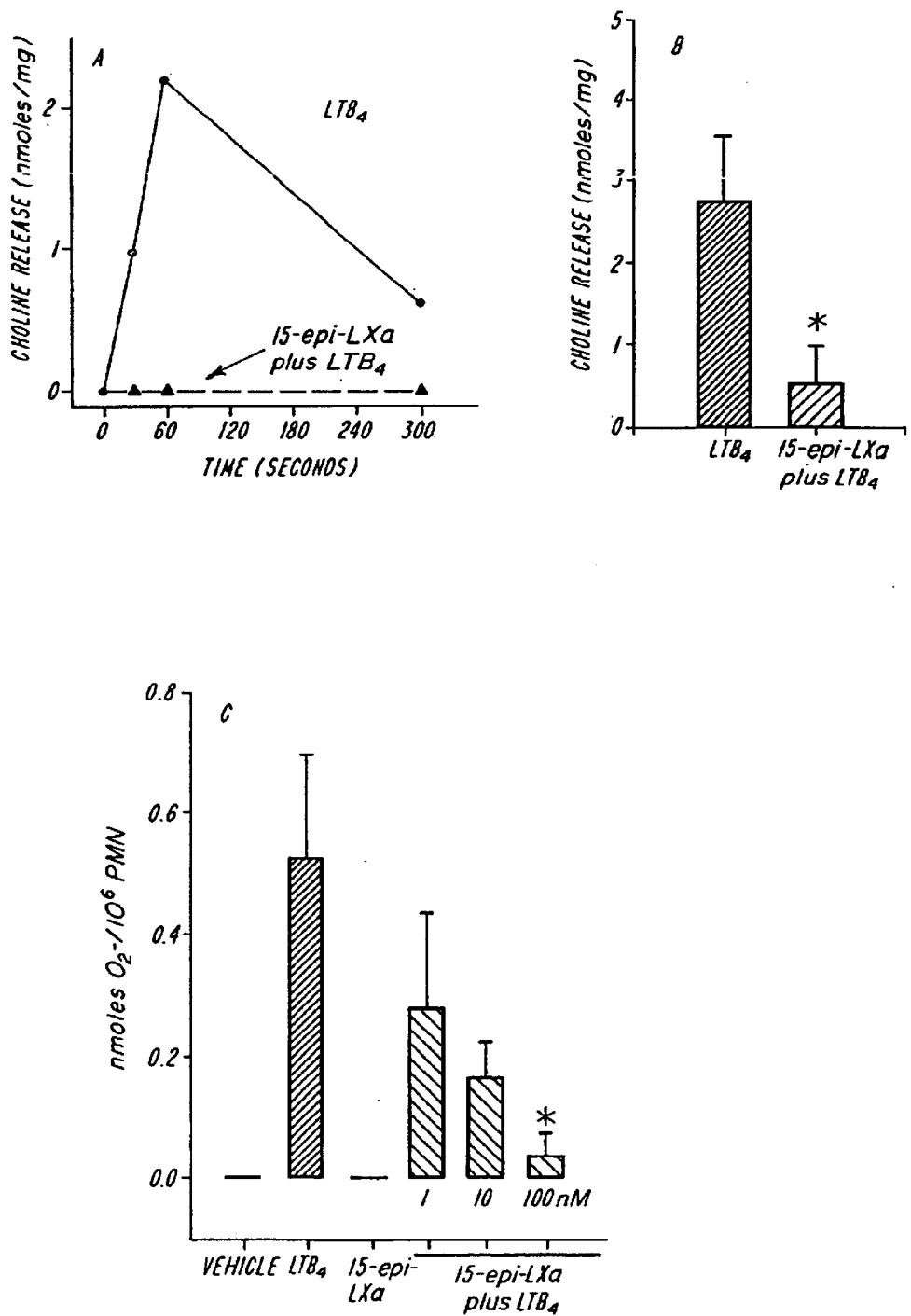
FIG. 2 demonstrates 15-epi-$LXA_4$ analog inhibits $LTB_4$-stimulated PLD activity and superoxide anion generation. Cell lysates (2–5×10$^6$ cells, 90–130 μg protein) were prepared from the same aliquots of PMN used to determine PSDP (see FIG. 1 & Methods), warmed to 37° C. and exposed to PC (2 mM in 50 mM Tris-HCl, pH 7.5, plus 30 mM $CaCl_2$). Reactions were terminated at 30 sec intervals and choline release was quantitated (26). Values in Panel A are representative (n=5, d=4) of the impact of 15-epi-LXa on choline release, and Panel B shows the change at 60 seconds (mean±S.E.). Superoxide anion generation by freshly isolated human PMN was determined (10 min, 37° C.) for $LTB_4$ (100 nM), 15-epi-LXa (100 nM), and increasing concentrations of 15-epi-LXa (1–100 nM, 5 min, 37° C.) followed by $LTB_4$ (100 nM, 10 min, 37° C.). Values reported in Panel C are the mean±S.E. for n=3 separate PMN donors. *P<0.05 by Student's t-test.

Because PLD activation occurs in vivo in the presence of many cofactors which modulate its activity, it was also determined the impact of PSDP on PLD activity in PMN lysates. Sixty seconds following LTB$_4$, PSDP levels decreased (28%, FIG. 1) and PLD activity was maximal (FIG. 2). Addition of PSDP (100 nM) to PMN lysates at this time (60 sec, LTB$_4$ 100 nM) gave 89.5+/−9.7% inhibition of PLD activity. Collectively, these results indicated that PSDP was a potent inhibitor of both plant and mammalian PLD's and establish a critical role for both the terminal phosphate and the isoprenoid chain length in PSDP's action with PLD activity.

The present results characterize PIPP remodeling as a rapid switch for "stop" signaling used by an extracellular regulator of PMN responses. LTB$_4$ receptor activation initiated a rapid and transient decrease in PSDP (FIG. 1) that coincided temporally with increased PLD activity (FIG. 2). As PSDP remodeling returned toward baseline values, PLD activity decreased, revealing an inverse relationship and suggesting a role for PSDP in the regulation of this pivotal lipid-modifying enzyme. Cells exposed to LTB$_4$ and an LXA$_4$ receptor agonist (15-epi-LXa) showed a dramatic switch in PSDP remodeling to give increased [$^{32}$P]-PSDP and marked inhibition of both PLD activity and superoxide anion generation (FIGS. 1 & 2). In addition, synthetic PSDP was a selective and potent inhibitor of isolated PLD (FIG. 3, Table I), a property not shared by other closely related lipids. Taken together, the reciprocal relationship between PSDP levels and PLD activity as well as direct inhibition of recombinant human PLD1b, purified cPLD and PLD activity in PMN lysates support a role for PSDP as an endogenous lipid regulator of PMN PLD activity. The different temporal profiles of PIPP remodeling initiated upon receptor activation by PMN ligands with opposing actions (i.e., stimulation and inhibition) suggest that PIPP remodeling and PSDP itself may serve as important components in intracellular signaling, in particular as "stop" signals.

Cholesterol is not a biosynthetic product in PMN, as they lack a mixed function oxidase and cyclase necessary for its endogenous formation from acetate (Shechter, I., Fogelman, A. M., and Popjak, G. (1980) A deficiency of mixed function oxidase activities in the cholesterol biosynthetic pathway of human granulocytes. *J. Lipid Res.* 21, 277–283). In view of the present findings, the resultant biosynthetic termination at squalene in PMN suggests that products such as squalene's direct precursor, PSDP, carries functions distinct from cholesterol biosynthesis. Hence, it is likely that the PIPP signaling pathway uncovered in human PMN may extend to other cell types. In addition to dietary influences known to impact mevalonate and polyisoprenyl phosphate biosynthesis, PSDP formation is also actively regulated by soluble immune stimuli and growth factors (FIG. 1B,C). Granulocyte/macrophage-colony stimulating factor, for example, increases PSDP remodeling in PMN whereas the chemotactic peptide, fMLP, triggers (within seconds) rapid decrements in PSDP and reciprocal increments in PSMP that return to baseline within 5–10 minutes (Levy, B. D., Petasis, N. A., and Serhan, C. N. (1997) Polyisoprenyl phosphates in intracellular signalling. *Nature* 389, 985–989). This time course of PIPP remodeling is similar in magnitude and extent to LTB$_4$-initiated decrements in PSDP (FIG. 1B & C) and correlates well with the time course of activating neutrophil responses such as O$_2^-$ generation, which is inhibited by PSDP. The presence of PSDP in peripheral blood PMN despite their inability to generate cholesterol from endogenous sources, its rapid remodeling in response to receptor-mediated inflammatory stimuli of diverse classes of receptor agonist, and its ability to inhibit PLD activity and NADPH oxidase at nanomolar levels are supportive evidence for a role for PSDP as a novel negative intracellular signal. Thus, this newly uncovered PIPP signaling might function to decrease negative signal levels, in contrast to the well-appreciated phosphotidylinositol signaling pathways (reviewed in Pettit, T. R., Martin, A., Horton, T., Liossis, C., Lord, J. M., and Wakelam, M. J. O. (1997) Diacylglycerol and phosphatidate generated by phospholipases C and D, respectively, have distinct fatty acid compositions and functions. *J. Biol. Chem.* 272, 17354–17359) that, when activated, rapidly generate positive intracellular stimuli (e.g., inositol trisphosphate, diacylglycerol & Ca$^{2+}$).

Aspirin, the lead non-steroidal anti-inflammatory drug, also effects cholesterol biosynthesis by mechanisms that remain to be completely elucidated (Rabinowitz, J. L., Baker, D. G., Villanueva, T. G., Asanza, A. P., and Capuzzi, D. M. (1992) Liver lipid profiles of adults taking therapeutic doses of aspirin. *Lipids* 27, 311–314). Beyond its well-appreciated inhibition of cyclooxygenase (COX), aspirin can pirate this system to set in place an anti-inflammatory circuit generating 15-epi-LX, carbon 15-R-epimers of the natural 15-S-containing-LX, during cell-cell interactions by aspirin-acetylated COX-2 and 5-lipoxygenase (FIG. 1A and Chiang, N., Takano, T., Clish, C. B., Petasis, N. A., Tai, H.-H., and Serhan, C. N. (1998) Aspirin-triggered 15-epi-lipoxin A$_4$ (ATL) generation by human leukocytes and murine peritonitis exudates: development of a specific 15-epi-LXA$_4$ ELISA. *J. Pharmacol Exper. Ther.* 287, 779–790). These aspirin-triggered LX carry anti-inflammatory and anti-proliferative properties (Claria, J., and Serhan, C. N. (1995) Aspirin triggers previously undescribed bioactive eicosanoids by human endothelial cell-leukocyte interactions. *Proc. Natl. Acad. Sci.* 92, 9475–9479; Serhan, C. N. (1997) Lipoxins and Novel Aspirin-Triggered 15-epi-Lipoxins: A Jungle of Cell-Cell Interactions or a Therapeutic Opportunity? *Prostaglandins* 53, 107–137) and may mediate a component of aspirin's beneficial therapeutic actions. As observed in the present experiments, $LXA_4$ receptor activation by a 15-epi-LX mimetic reversed PSDP remodeling initiated by $LTB_4$ receptors, leading to increases in PSDP levels (FIG. 1). Since the 15-epi-LXa inhibited both PLD activity and superoxide anion generation (FIG. 2), these results implicate PIPP remodeling as a component of the cellular basis for aspirin's inhibition of excessive inflammatory responses. In addition to regulating $LTB_4$'s stimulatory actions, this novel mechanism of inhibition of $LTB_4$ receptor signaling may also play broader roles in host defense, as this receptor was recently identified as a co-receptor for HIV-1 (Owman, C., Garzino-Demo, A., Cocchi, F., Popovic, M., Sabirsh, A., and Gallo, R. (1998) The leukotriene $B_4$ receptor functions as a novel type of coreceptor mediating entry of primary HIV-1 isolates into CD4-positive cells. *Proc. Natl. Acad. Sci.* 95, 9530–9534).

Hydrolysis of PC to PA by PLD appears crucial in transmembrane signaling by a wide range of receptor classes during PMN activation (Olson, S. C., and Lambeth, J. D. (1996) Biochemistry and cell biology of phospholipase D in human neutrophils. *Chem. Phys. Lipids* 80, 3–19). Both G-protein linked receptors and receptor tyrosine kinases activate PLD. In leukocytes, several factors including $PKC\alpha$ (in a kinase-independent manner) and increased intracellular calcium can activate PLD1 (Exton, J. H. (1997) New developments in phospholipase D. *J. Biol. Chem.* 272, 15579–15582). FMLP-stimulated PLD activity in PMN is increased by membrane association of the ADP-ribosylation factor (ARF) and small GTPase RhoA (Fensome, A., Whatmore, J., Morgan, C., Jones, D., and Cockcroft, S. (1998) ADP-ribosylation factor and Rho proteins mediate fALP-dependent activation of phospholipase D in human neutrophils. *J. Biol. Chem.* 273, 13157–13164). Of considerable interest here, PSDP directly inhibited recombinant hPLD1b in the absence of regulatory proteins (see Table I). These results suggest that PSDP may inhibit PLD at its catalytic center and is likely to act at other PLD isoforms, such as PLD1a and PLD2 isoforms where the catalytic centers are conserved. PSDP's ability to serve as an endogenous inhibitor of PLD likely results from PSDP's unique three-dimensional and physical chemical properties which might now serve as a template for the preparation of more potent PLD inhibitors by design to fulfill the structure activity relationship uncovered here.

Regulation of PMN activation in complex host responses is controlled in part by soluble mediators and, in particular, by autacoids with opposing actions (Serhan, C. N., Haeggstrom, J. Z., and Leslie, C. C. (1996) Lipid mediator networks in cell signaling: update and impact of cytokines. *FASEB J.* 10, 1147–1158), such as LT and LX, that here gave markedly different profiles for PIPP remodeling (FIG. 1). In most cell types, PSDP is appreciated as a biosynthetic intermediate in cholesterol production by microsomal squalene synthase, which catalyzes head-to-head condensation of two FDP (Jarstfer, M. B., Blagg, B. S. J., Rogers, D. H., and Poulter, C. D. (1996) Biosynthesis of squalene. Evidence for a tertiary cyclopropylcarbinyl cationic intermediate in the rearrangement of presqualene diphosphate to squalene. *J. Amer. Chem. Soc.* 118, 13089–13090). Ligand-operated rapid remodeling of PSDP in PMN is likely to occur in membranes in proximity to $LTB_4$ and $LXA_4$ receptors and suggests a non-microsomal pool of PSDP that may result from 1) novel biosynthetic and/or metabolic pathways or 2) intracellular trafficking of PIPP with proteins from endoplasmic reticulum to membrane domains. Incorporation of $[^{32}P]$ from ATP into PSDP but not FDP (see Results) is further evidence in support of a novel route for PSDP formation in PMN. The present results suggest that PIPP remodeling is linked to cell surface receptor activation and is involved in the intracellular transmission of extracellular ligands with opposing biological actions. In the present working model, a "negative lipid signal" (i.e., PSDP) is held at a set point, like a ratchet, in "resting" cells. Incoming positive signals ($LTB_4$, fMLP, etc.) initiate the degradation and inactivation of this inhibitory lipid (e.g., remodeling PSDP to the inactive monophosphate species, PSMP) (FIG. 1A and ref 22). Thus, PIPP remodeling enables mounting of intracellular positive signals that threshold for activation of select cellular processes. This type of signaling may explain the selectivity and tight coupling required by agonists such as $LTB_4$ that stimulate highly specialized functional responses of PMN such as chemotaxis, granule mobilization and superoxide anion generation. The extent to which this model of cell signaling, namely receptor-initiated degradation of negative lipid signals, occurs with other receptors and cell types remains for further studies.

In summary, ligand-operated rapid remodeling of PIPPs in human PMN and direct inhibition of PLD activity at nanomolar levels support a role for PSDP as an intracellular signal and provide novel intracellular targets by which PSDP can regulate cellular responses (Levy, B. D., Petasis, N. A., and Serhan, C. N. (1997) Polyisoprenyl phosphates in intracellular signalling. *Nature* 389, 985–989). Given the wide occurrence of PIPP and critical role of PLD in the plant and animal kingdoms, PIPP remodeling and direct inhibition of PLD first established here in human PMN may have wider implications in cell signaling in other cell types and species (Martin, A., Saqib, K. M., Hodgkin, M. N., Brown, F. D., Pettit, T. R., Armstrong, S., and Wakelam, M. J. O. (1997) Role and regulation of phospholipase D signalling. *Biochem. Soc. Trans.* 25, 1157–1160; Bach, T. J. (1995) Some new aspects of isoprenoid biosynthesis in plants—a review. *Lipids* 30, 191–202). The present results are the first to show direct inhibition of a phospholipase involved in signal transduction by an endogenous intracellular lipid and set forth a new paradigm for lipid-protein interactions in the control of cellular responses, namely receptor-initiated degradation of a repressor lipid, that is also subject to regulation by aspirin ingestion via the actions of aspirin-triggered 15-epimer LX. Together, these results suggest that PIPP signaling pathways might also be of interest in pharmacologic interventions and specifically that the conformation of PSDP can serve as a template for design of novel inhibitors.

REFERENCES

1. Weissmann, G., Smolen, J. E., and Korchak, H. M. (1980) Release of inflammatory mediators from stimulated neutrophils. *N. Engl. J. Med.* 303, 27–34
2. Serhan, C. N., Haeggstrom, J. Z., and Leslie, C. C. (1996) Lipid mediator networks in cell signaling: update and impact of cytokines. *FASEB J.* 10, 1147–1158
3. Weiss, S. J. (1989) Tissue destruction by neutrophils. *N. Engl. J. Med.* 320, 365–376
4. Serhan, C. N. (1994) Lipoxin biosynthesis and its impact in inflammatory and vascular events. *Biochim. Biophys. Acta* 1212, 1–25
5. Borgeat, P., and Naccache, P. H. (1990) Biosynthesis and biological activity of leukotriene $B_4$. *Clin. Biochem.* 23, 459–468

6. Yokomizo, T., Izumi, T., Chang, K., Takuwa, T., and Shimizu, T. (1997) A G-protein-coupled receptor for leukotriene B$_4$ that mediates chemotaxis. *Nature* 387, 620–624
7. Fiore, S., Romano, M., Reardon, E. M., and Serhan, C. N. (1993) Induction of functional lipoxin A$_4$ receptors in HL-60 cells. *Blood* 81, 3395–3403
8. Isakson, P., Seibert, K., Masferrer, J., Salvemini, D., Lee, L., and Needleman, P. (1995) Discovery of a better aspirin. *Advances in Prostaglandin, Thromboxane & Leukotriene Research* 23, 49–54
9. Chiang, N., Takano, T., Clish, C. B., Petasis, N. A., Tai, H.-H., and Serhan, C. N. (1998) Aspirin-triggered 15-epi-lipoxin A$_4$ (ATL) generation by human leukocytes and murine peritonitis exudates: development of a specific 15-epi-LXA$_4$ ELISA. *J. Pharmacol Exper. Ther.* 287, 779–790
10. Serhan, C. N., Maddox, J. F., Petasis, N. A., Akritopoulou-Zanze, I., Papayianni, A., Brady, H. R., Colgan, S. P., and Madara, J. L. (1995) Design of lipoxin A$_4$ stable analogs that block transmigration and adhesion of human neutrophils. *Biochemistry* 34, 14609–14615
11. Takano, T., Fiore, S., Maddox, J. F., Brady, H. R., Petasis, N. A., and Serhan, C. N. (1997) Aspirin-triggered 15-epi-lipoxin A$_4$ (LXA$_4$) and LXA$_4$ Stable analogues are potent inhibitors of acute inflammation: Evidence for anti-inflammatory receptors. *J. Exp. Med.* 185, 1693–1704
12. Owman, C., Garzino-Demo, A., Cocchi, F., Popovic, M., Sabirsh, A., and Gallo, R. (1998) The leukotriene B$_4$receptor functions as a novel type of coreceptor mediating entry of primary HIV-1 isolates into CD4-positive cells. *Proc. Natl. Acad. Sci.* 95, 9530–9534
13. Marcus, A. J. (1995) Aspirin as prophylaxis against colorectal cancer. *N. Engl. J. Med.* 333, 656–658
14. Vainio, H., and Morgan, G. (1997) Aspirin for the second hundred years: new uses for an old drug. *Pharmacol Toxicol* 81, 151–152
15. Herschman, H. R. (1998) Recent progress in the cellular and molecular biology of prostaglandin synthesis. *Trends in Cardiovasc. Med.* 8, 145–150
16. Takano, T., Clish, C. B., Gronert, K., Petasis, N., and Serhan, C. N. (1998) Neutrophil-mediated changes in vascular permeability are inhibited by topical application of aspirin-triggered 15-epi-lipoxin A$_4$ and novel lipoxin B$_4$ stable analogues. *J. Clin. Invest.* 101, 819–826
17. Billah, M. M., Eckel, S., Mullmann, T. J., Egan, R. W., and Siegel, M. I. (1989) Phosphatidylcholine hydrolysis by phospholipase D determines phosphatidate and diglyceride levels in chemotactic peptide-stimulated human neutrophils. Involvement of phsophatidate phosphohydrolase in signal transduction. *J. Biol. Chem.* 264, 17069–17077
18. Wakelarn, M. J. O., Martin, A., Hodgkin, M. N., Brown, F., Pettit, T. R., Cross, M. J., De Takats, P. G., and Reynolds, J. L. (1997) Role and regulation of phospholipase D activity in normal and cancer cells. *Advances in Enzyme Regulation* 37, 29–34
19. Olson, S. C., and Lambeth, J. D. (1996) Biochemistry and cell biology of phospholipase D in human neutrophils. *Chem. Phys. Lipids* 80, 3–19
20. Steed, P. M., Clark, K. L., Boyar, W. C., and Lasala, D. J. (1998) Characterization of human PLD2 and the analysis of PLD isoform splice variants. *FASEB J.* 12, 1309–1317
21. Martin, A., Saqib, K. M., Hodgkin, M. N., Brown, F. D., Pettit, T. R., Armstrong, S., and Wakelam, M. J. O. (1997) Role and regulation of phospholipase D signalling. *Biochem. Soc. Trans.* 25, 1157–1160
22. Levy, B. D., Petasis, N. A., and Serhan, C. N. (1997) Polyisoprenyl phosphates in intracellular signalling. *Nature* 389, 985–989
23. Agwu, D. E., McPhail, L. C., Sozzani, S., Bass, D. A., and McCall, C. E. (1991) Phosphatidic acid as a second messenger in human polymorphonuclear leukocytes. Effects on activation of NADPH oxidase. *J. Clin. Invest.* 88, 531–539
24. Pettit, T. R., Martin, A., Horton, T., Liossis, C., Lord, J. M., and Wakelarn, M. J. O. (1997) Diacylglycerol and phosphatidate generated by phospholipases C and D, respectively, have distinct fatty acid compositions and functions. *J. Biol. Chem.* 272, 17354–17359
25. Gomez-Cambronero, J. (1995) Immunoprecipitation of a phospholipase D activity with antiphosphotyrosine antibodies. *J. Interferon Cytokine Res.* 15, 877–885
26. Abousalham, A., Riviere, M., Teissere, M., and Verger, R. (1993) Improved purification and biochemical characterization of phospholipase D from cabbage. *Biochim. Biophys. Acta* 1158,1–7
27. Zhou, H.-L., Chabot-Fletcher, M., Foley, J. J., Sarau, H. M., Tzimas, M. N., Winkler, J. D., and Torphy, T. J. (1993) Association between leukotriene B$_4$-induced phospholipase D activation and degranulation of human neutrophils. *Biochem. Pharmacol.* 46, 139–148
28. Shechter, I., Fogelman, A. M., and Popjak, G. (1980) A deficiency of mixed function oxidase activities in the cholesterol biosynthetic pathway of human granulocytes. *J. Lipid Res.* 21, 277–283
29. Rabinowitz, J. L., Baker, D. G., Villanueva, T. G., Asanza, A. P., and Capuzzi, D. M. (1992) Liver lipid profiles of adults taking therapeutic doses of aspirin. *Lipids* 27, 311–314
30. Claria, J., and Serhan, C. N. (1995) Aspirin triggers previously undescribed bioactive eicosanoids by human endothelial cell-leukocyte interactions. *Proc. Natl. Acad. Sci.* 92, 9475–9479
31. Serhan, C. N. (1997) Lipoxins and Novel Aspirin-Triggered 15-epi-Lipoxins: A Jungle of Cell-Cell Interactions or a Therapeutic Opportunity? *Prostaglandins* 53, 107–137
32. Exton, J. H. (1997) New developments in phospholipase D. *J. Biol. Chem.* 272, 15579–15582
33. Fensome, A., Whatmore, J., Morgan, C., Jones, D., and Cockcroft, S. (1998) ADP-ribosylation factor and Rho proteins mediate fMLP-dependent activation of phospholipase D in human neutrophils. *J. Biol. Chem.* 273, 13157–13164
34. Jarstfer, M. B., Blagg, B. S. J., Rogers, D. H., and Poulter, C. D. (1996) Biosynthesis of squalene. Evidence for a tertiary cyclopropylcarbinyl cationic intermediate in the rearrangement of presqualene diphosphate to squalene. *J. Amer. Chem. Soc.* 118, 13089–13090
35. Bach, T. J. (1995) Some new aspects of isoprenoid biosynthesis in plants—a review. *Lipids* 30, 191–202

One having ordinary skill in the art will appreciate further features and advantages of the invention based on the above-described embodiments. Accordingly, the invention is not to be limited by what has been particularly shown and described, except as indicated by the appended claims. All publications and references cited herein, including those in the background section, are expressly incorporated herein by reference in their entirety.

What is claimed is:

1. A method for treating phospholipase D (PLD) initiated polymorphoneutrophil (PMN) inflammation in a subject, comprising administering to the subject an effective anti-inflammatory amount of a lipoxin analog having the formula

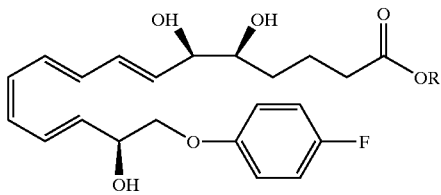

wherein R is a hydrogen atom, a pharmaceutically acceptable ester and pharmaceutically acceptable salts thereof, such that PLD initiated polymorphoneutrophil (PMN) inflammation is treated in a subject.

2. The method of claim 1, wherein said method is performed in vitro.

3. The method of claim 1, wherein said method is performed in vivo.

4. A method for treating phospholipase D (PLD) initiated superoxide generation or degranulation in a subject, comprising administering to the subject an effective anti-PLD amount of a lipoxin analog having the formula

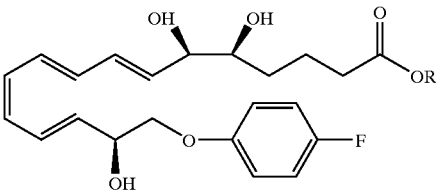

wherein R is a hydrogen atom, a pharmaceutically acceptable ester and pharmaceutically acceptable salts thereof, such that PLD initiated superoxide generation or granulation is treated in a subject.

5. The method of claim 4, wherein said method is performed in vitro.

6. The method of claim 4, wherein said method is performed in vivo.

* * * * *